(12) United States Patent
Gerberding

(10) Patent No.: US 10,004,510 B2
(45) Date of Patent: Jun. 26, 2018

(54) SYSTEMS AND METHODS FOR ENCLOSING AN ANATOMICAL OPENING, INCLUDING SHOCK ABSORBING ANEURYSM DEVICES

(75) Inventor: Brent Gerberding, San Jose, CA (US)

(73) Assignee: PULSAR VASCULAR, INC., Los Gatos, CA (US)

( * ) Notice: Subject to any disclaimer, the term of this patent is extended or adjusted under 35 U.S.C. 154(b) by 352 days.

(21) Appl. No.: 14/130,727

(22) PCT Filed: Jun. 1, 2012

(86) PCT No.: PCT/US2012/040552
§ 371 (c)(1),
(2), (4) Date: Apr. 30, 2014

(87) PCT Pub. No.: WO2012/167150
PCT Pub. Date: Dec. 6, 2012

(65) Prior Publication Data
US 2014/0236216 A1    Aug. 21, 2014

Related U.S. Application Data

(60) Provisional application No. 61/493,348, filed on Jun. 3, 2011.

(51) Int. Cl.
*A61M 29/00*     (2006.01)
*A61B 17/12*     (2006.01)
(Continued)

(52) U.S. Cl.
CPC .. *A61B 17/12113* (2013.01); *A61B 17/12022* (2013.01); *A61B 17/12118* (2013.01);
(Continued)

(58) Field of Classification Search
CPC ........ A61B 17/12022; A61B 17/12118; A61B 17/12113; A61B 17/12172;
(Continued)

(56) References Cited

U.S. PATENT DOCUMENTS 3,868,956 A    3/1975    Alfidi et al.
4,164,045 A    8/1979    Bokros et al.
(Continued)

FOREIGN PATENT DOCUMENTS

AU    2006304660 A1    4/2007
CN    1384726          12/2002
(Continued)

OTHER PUBLICATIONS

Cordis NeuroVascular, Inc.; "Masstransit Microcatheter," Product Prochure; No. 153-8383-3; Miami Lakes, FL, USA (2003).
(Continued)

*Primary Examiner* — Jing Ou
(74) *Attorney, Agent, or Firm* — Troutman Sanders LLP

(57) ABSTRACT

The present technology relates to systems and methods for enclosing an anatomical opening, including shock absorbing aneurysm devices. In some embodiments, the systems include a closure structure comprising a distal-facing aspect configured to at least partially occlude the aneurysm and a supplemental stabilizer connected to the closure structure. The supplemental stabilizer can be configured to reside in a parent artery and press outward against a luminal wall thereof. The systems can further include a shock absorbing structure coupled to a proximal end portion of the closure structure and to a distal end portion of the supplemental stabilizer. The shock absorbing structure can inhibit movement or dislodgement of the closure structure or the supplemental stabilizer relative to the aneurysm.

12 Claims, 4 Drawing Sheets

(51) Int. Cl.
*A61F 2/86* (2013.01)
*A61F 2/82* (2013.01)

(52) U.S. Cl.
CPC .......... *A61F 2/86* (2013.01); *A61B 17/12145* (2013.01); *A61B 17/12172* (2013.01); *A61F 2002/823* (2013.01); *A61F 2230/0026* (2013.01); *A61F 2230/0095* (2013.01)

(58) Field of Classification Search
CPC ................ A61B 17/12145; A61F 2/86; A61F 2230/0026; A61F 2002/823; A61F 2230/0095
See application file for complete search history.

(56) References Cited

U.S. PATENT DOCUMENTS

| | | |
|---|---|---|
| 4,248,234 A | 2/1981 | Assenza et al. |
| 4,645,495 A | 2/1987 | Vaillancourt |
| 4,651,751 A | 3/1987 | Swendson et al. |
| 4,665,906 A | 5/1987 | Jervis |
| 4,706,671 A | 11/1987 | Weinrib |
| 4,710,192 A | 12/1987 | Liotta et al. |
| 4,739,768 A | 4/1988 | Engelson |
| 4,820,298 A | 4/1989 | Leveen et al. |
| 4,873,978 A | 10/1989 | Ginsburg |
| 4,909,787 A | 3/1990 | Danforth |
| 4,994,069 A | 2/1991 | Ritchart et al. |
| 5,011,488 A | 4/1991 | Ginsburg |
| 5,074,869 A | 12/1991 | Daicoff |
| 5,122,136 A | 6/1992 | Guglielmi et al. |
| 5,226,911 A | 7/1993 | Chee et al. |
| 5,250,071 A | 10/1993 | Palermo |
| 5,261,916 A | 11/1993 | Engelson |
| 5,263,964 A | 11/1993 | Purdy |
| 5,263,974 A | 11/1993 | Matsutani et al. |
| 5,271,414 A | 12/1993 | Partika et al. |
| 5,304,195 A | 4/1994 | Twyford, Jr. et al. |
| 5,334,168 A | 8/1994 | Hemmer |
| 5,342,386 A | 8/1994 | Trotta |
| 5,350,397 A | 9/1994 | Palermo et al. |
| 5,354,295 A | 10/1994 | Guglielmi et al. |
| 5,527,338 A | 6/1996 | Purdy |
| 5,531,685 A | 7/1996 | Hemmer et al. |
| 5,578,074 A | 11/1996 | Mirigian |
| 5,624,449 A | 4/1997 | Pham et al. |
| 5,643,254 A | 7/1997 | Scheldrup et al. |
| 5,665,106 A | 9/1997 | Hammerslag |
| 5,669,931 A | 9/1997 | Kupiecki et al. |
| 5,693,067 A | 12/1997 | Purdy |
| 5,733,294 A | 3/1998 | Forber et al. |
| 5,733,329 A | 3/1998 | Wallace et al. |
| 5,749,890 A | 5/1998 | Shaknovich |
| 5,749,894 A | 5/1998 | Engelson |
| 5,759,194 A | 6/1998 | Hammerslag |
| 5,766,192 A | 6/1998 | Zacca |
| 5,769,884 A | 6/1998 | Solovay |
| 5,797,953 A | 8/1998 | Tekulve |
| 5,814,062 A | 9/1998 | Sepetka et al. |
| 5,843,103 A | 12/1998 | Wulfman |
| D407,818 S | 4/1999 | Mariant et al. |
| 5,895,391 A | 4/1999 | Farnholtz |
| 5,895,410 A | 4/1999 | Forber et al. |
| 5,910,145 A | 6/1999 | Fischell et al. |
| 5,911,737 A | 6/1999 | Lee et al. |
| 5,916,235 A | 6/1999 | Guglielmi |
| 5,925,060 A | 7/1999 | Forber |
| 5,925,062 A | 7/1999 | Purdy |
| 5,925,683 A | 7/1999 | Park |
| 5,928,260 A | 7/1999 | Chin et al. |
| 5,933,329 A | 8/1999 | Tijanoc et al. |
| 5,935,114 A | 8/1999 | Jang et al. |
| 5,935,148 A | 8/1999 | Villar et al. |
| 5,951,599 A | 9/1999 | McCrory |
| 5,968,068 A | 10/1999 | Dehdashtian et al. |
| 5,980,514 A | 11/1999 | Kupiecki et al. |
| 5,980,554 A | 11/1999 | Lenker et al. |
| 5,984,944 A | 11/1999 | Forber |
| 6,007,544 A | 12/1999 | Kim |
| 6,013,055 A | 1/2000 | Bampos et al. |
| 6,022,341 A | 2/2000 | Lentz |
| 6,036,720 A | 3/2000 | Abrams et al. |
| 6,063,070 A | 5/2000 | Eder |
| 6,063,104 A | 5/2000 | Villar et al. |
| 6,071,263 A | 6/2000 | Kirkman |
| 6,077,291 A | 6/2000 | Das |
| 6,081,263 A | 6/2000 | LeGall et al. |
| 6,090,125 A | 7/2000 | Horton |
| 6,093,199 A | 7/2000 | Brown et al. |
| 6,096,021 A | 8/2000 | Helm et al. |
| 6,096,034 A | 8/2000 | Kupiecki et al. |
| 6,102,917 A | 8/2000 | Maitland et al. |
| 6,110,191 A | 8/2000 | Dehdashtian et al. |
| 6,117,157 A | 9/2000 | Tekulve |
| 6,139,564 A | 10/2000 | Teoh |
| 6,146,339 A | 11/2000 | Biagtan et al. |
| 6,152,944 A | 11/2000 | Holman et al. |
| 6,168,615 B1 | 1/2001 | Ken et al. |
| 6,168,622 B1 | 1/2001 | Mazzocchi |
| 6,174,322 B1 | 1/2001 | Schneidt |
| 6,183,495 B1 | 2/2001 | Lenker et al. |
| 6,193,708 B1 | 2/2001 | Ken et al. |
| RE37,117 E | 3/2001 | Palermo |
| 6,221,066 B1 | 4/2001 | Ferrera et al. |
| 6,221,086 B1 | 4/2001 | Forber |
| 6,224,610 B1 | 5/2001 | Ferrera |
| 6,228,052 B1 | 5/2001 | Pohndorf |
| 6,261,305 B1 | 7/2001 | Marotta et al. |
| 6,293,960 B1 | 9/2001 | Ken |
| 6,296,622 B1 | 10/2001 | Kurz et al. |
| 6,309,367 B1 | 10/2001 | Boock |
| 6,325,807 B1 | 12/2001 | Que |
| 6,344,041 B1 | 2/2002 | Kupiecki et al. |
| 6,344,048 B1 | 2/2002 | Chin et al. |
| 6,361,558 B1 | 3/2002 | Hieshima et al. |
| 6,375,668 B1 | 4/2002 | Gifford et al. |
| 6,383,174 B1 | 5/2002 | Eder |
| 6,398,791 B1 | 6/2002 | Que et al. |
| 6,478,773 B1 | 11/2002 | Gandhi et al. |
| 6,491,711 B1 | 12/2002 | Durcan |
| 6,517,515 B1 | 2/2003 | Eidenschink |
| 6,530,935 B2 | 3/2003 | Wensel et al. |
| 6,533,905 B2 | 3/2003 | Johnson et al. |
| 6,554,794 B1 | 4/2003 | Mueller et al. |
| 6,589,256 B2 | 7/2003 | Forber |
| 6,592,605 B2 | 7/2003 | Lenker et al. |
| 6,613,074 B1 * | 9/2003 | Mitelberg ........ A61B 17/12022 606/200 |
| 6,616,681 B2 | 9/2003 | Hanson et al. |
| 6,626,889 B1 | 9/2003 | Simpson et al. |
| 6,626,928 B1 | 9/2003 | Raymond et al. |
| 6,638,268 B2 | 10/2003 | Niazi |
| 6,652,556 B1 | 11/2003 | VanTassel et al. |
| 6,663,607 B2 | 12/2003 | Slaikeu et al. |
| 6,663,648 B1 | 12/2003 | Trotta |
| 6,669,795 B2 | 12/2003 | Johnson et al. |
| 6,672,338 B1 | 1/2004 | Esashi et al. |
| 6,679,836 B2 | 1/2004 | Couvillon, Jr. |
| 6,679,903 B2 | 1/2004 | Kurz |
| 6,689,141 B2 | 2/2004 | Ferrera et al. |
| 6,694,979 B2 | 2/2004 | Deem et al. |
| 6,723,112 B2 | 4/2004 | Ho et al. |
| 6,740,073 B1 | 5/2004 | Saville |
| 6,740,277 B2 | 5/2004 | Howell et al. |
| 6,746,468 B1 | 6/2004 | Sepetka et al. |
| 6,780,196 B2 | 8/2004 | Chin et al. |
| 6,790,218 B2 | 9/2004 | Jayaraman |
| 6,802,851 B2 | 10/2004 | Jones et al. |
| 6,811,560 B2 | 11/2004 | Jones et al. |
| 6,824,553 B1 | 11/2004 | Samson et al. |
| 6,835,185 B2 | 12/2004 | Ramzipoor et al. |
| 6,837,870 B2 | 1/2005 | Duchamp |
| 6,843,802 B1 | 1/2005 | Villalobos et al. |
| 6,855,153 B2 | 2/2005 | Saadat |

(56) References Cited

U.S. PATENT DOCUMENTS

| | | |
|---|---|---|
| 6,863,678 B2 | 3/2005 | Lee et al. |
| 6,890,218 B2 | 5/2005 | Patwardhan et al. |
| 6,911,037 B2 | 6/2005 | Gainor et al. |
| 6,936,055 B1 | 8/2005 | Ken et al. |
| 6,939,055 B2 | 9/2005 | Durrant et al. |
| 6,986,774 B2 | 1/2006 | Middleman et al. |
| 6,994,092 B2 | 2/2006 | van der Burg et al. |
| 7,011,094 B2 | 3/2006 | Rapacki et al. |
| 7,033,374 B2 | 4/2006 | Schaefer et al. |
| 7,033,387 B2 | 4/2006 | Zadno-Azizi et al. |
| 7,122,043 B2 | 10/2006 | Greenhalgh et al. |
| 7,147,659 B2 | 12/2006 | Jones |
| 7,156,871 B2 | 1/2007 | Jones et al. |
| 7,169,177 B2 | 1/2007 | Obara |
| 7,229,461 B2 | 6/2007 | Chin et al. |
| 7,232,461 B2 | 6/2007 | Ramer |
| 7,267,679 B2 | 9/2007 | McGuckin, Jr. et al. |
| 7,306,622 B2 | 12/2007 | Jones et al. |
| 7,322,960 B2 | 1/2008 | Yamamoto et al. |
| 7,343,856 B2 | 3/2008 | Blohdorn |
| 7,387,629 B2 | 6/2008 | Vanney et al. |
| 7,410,482 B2 | 8/2008 | Murphy et al. |
| 7,569,066 B2 | 8/2009 | Gerberding et al. |
| 7,608,088 B2 | 10/2009 | Jones et al. |
| 7,662,168 B2 | 2/2010 | McGuckin, Jr. et al. |
| 7,857,825 B2 | 12/2010 | Moran et al. |
| 7,892,254 B2 | 2/2011 | Klint et al. |
| 8,016,853 B2 | 9/2011 | Griffen et al. |
| 8,075,585 B2 | 12/2011 | Lee et al. |
| 8,187,315 B1 | 5/2012 | Clauson et al. |
| 8,262,692 B2 | 9/2012 | Rudakov |
| 8,388,650 B2 | 3/2013 | Gerberding et al. |
| 8,444,667 B2 | 5/2013 | Porter |
| 8,470,013 B2 | 6/2013 | Duggal et al. |
| 8,540,763 B2 | 9/2013 | Jones et al. |
| 8,545,530 B2 | 10/2013 | Eskridge et al. |
| 8,551,132 B2 | 10/2013 | Eskridge et al. |
| 8,556,953 B2 | 10/2013 | Berez et al. |
| 8,715,312 B2 | 5/2014 | Burke et al. |
| 8,715,338 B2 | 5/2014 | Frid |
| 8,728,141 B2 | 5/2014 | Riina et al. |
| 8,747,430 B2 | 6/2014 | Porter |
| 8,771,341 B2 | 7/2014 | Strauss et al. |
| 8,915,950 B2 | 12/2014 | Cam et al. |
| 8,926,680 B2 | 1/2015 | Ferrera et al. |
| 8,956,399 B2 | 2/2015 | Cam et al. |
| 8,979,893 B2 | 3/2015 | Gerberding et al. |
| 9,060,886 B2 | 6/2015 | Molaei et al. |
| 9,107,670 B2 | 8/2015 | Hannes et al. |
| 9,119,625 B2 | 9/2015 | Bachman et al. |
| 9,179,918 B2 | 11/2015 | Levy et al. |
| 9,186,267 B2 | 11/2015 | Losordo et al. |
| 9,192,388 B2 | 11/2015 | Cam et al. |
| 9,211,124 B2 | 12/2015 | Campbell et al. |
| 9,259,229 B2 | 2/2016 | Abrams et al. |
| 9,277,924 B2 | 3/2016 | Clarke et al. |
| 2002/0026232 A1 | 2/2002 | Marotta et al. |
| 2003/0033003 A1* | 2/2003 | Harrison ............... A61F 2/91 623/1.15 |
| 2003/0057156 A1 | 3/2003 | Peterson et al. |
| 2003/0139802 A1 | 7/2003 | Wulfman et al. |
| 2003/0181922 A1 | 9/2003 | Alferness |
| 2003/0181942 A1 | 9/2003 | Sutton et al. |
| 2003/0195385 A1 | 10/2003 | DeVore |
| 2003/0195553 A1 | 10/2003 | Wallace et al. |
| 2003/0212412 A1 | 11/2003 | Dillard et al. |
| 2004/0044391 A1 | 3/2004 | Porter |
| 2004/0068314 A1 | 4/2004 | Jones et al. |
| 2004/0087998 A1 | 5/2004 | Lee et al. |
| 2004/0111112 A1 | 6/2004 | Hoffmann |
| 2004/0158311 A1 | 8/2004 | Berhow et al. |
| 2004/0167597 A1 | 8/2004 | Constantino et al. |
| 2004/0167602 A1 | 8/2004 | Fischell et al. |
| 2004/0172056 A1 | 9/2004 | Guterman et al. |
| 2004/0193246 A1 | 9/2004 | Ferrera |
| 2004/0210248 A1 | 10/2004 | Gordon et al. |
| 2004/0210298 A1 | 10/2004 | Rabkin et al. |
| 2005/0021023 A1 | 1/2005 | Guglielmi et al. |
| 2005/0025797 A1 | 2/2005 | Wang et al. |
| 2005/0033349 A1* | 2/2005 | Jones ............... A61B 17/12022 606/200 |
| 2005/0033409 A1* | 2/2005 | Burke ............... A61B 17/12022 623/1.15 |
| 2005/0096728 A1 | 5/2005 | Ramer |
| 2005/0177224 A1 | 8/2005 | Fogarty et al. |
| 2006/0004436 A1 | 1/2006 | Amarant et al. |
| 2006/0030929 A1 | 2/2006 | Musbach |
| 2006/0052862 A1 | 3/2006 | Kanamaru et al. |
| 2006/0058837 A1 | 3/2006 | Bose et al. |
| 2006/0064151 A1 | 3/2006 | Guterman et al. |
| 2006/0106418 A1 | 5/2006 | Seibold et al. |
| 2006/0200234 A1 | 9/2006 | Hines |
| 2006/0206199 A1 | 9/2006 | Churchwell et al. |
| 2006/0247680 A1 | 11/2006 | Amplatz et al. |
| 2006/0259131 A1 | 11/2006 | Molaei et al. |
| 2006/0264905 A1 | 11/2006 | Eskridge et al. |
| 2006/0264907 A1 | 11/2006 | Eskridge et al. |
| 2007/0067015 A1 | 3/2007 | Jones et al. |
| 2007/0088387 A1 | 4/2007 | Eskridge et al. |
| 2007/0106311 A1 | 5/2007 | Wallace et al. |
| 2007/0191884 A1 | 8/2007 | Eskridge et al. |
| 2007/0198075 A1 | 8/2007 | Levy |
| 2007/0203567 A1 | 8/2007 | Levy |
| 2007/0270902 A1 | 11/2007 | Slazas et al. |
| 2008/0004653 A1 | 1/2008 | Sherman et al. |
| 2008/0004692 A1 | 1/2008 | Henson et al. |
| 2008/0039930 A1 | 2/2008 | Jones et al. |
| 2008/0147100 A1 | 6/2008 | Wallace |
| 2008/0183143 A1 | 7/2008 | Palisis et al. |
| 2008/0221600 A1 | 9/2008 | Dieck et al. |
| 2008/0269774 A1 | 10/2008 | Garcia et al. |
| 2008/0319533 A1 | 12/2008 | Lehe |
| 2009/0069880 A1 | 3/2009 | Vonderwalde et al. |
| 2009/0125053 A1 | 5/2009 | Ferrera et al. |
| 2009/0306678 A1 | 12/2009 | Hardert et al. |
| 2010/0023105 A1 | 1/2010 | Levy et al. |
| 2010/0063531 A1 | 3/2010 | Rudakov et al. |
| 2010/0094335 A1 | 4/2010 | Gerberding et al. |
| 2011/0022149 A1* | 1/2011 | Cox ............... A61B 17/12118 623/1.11 |
| 2011/0270373 A1 | 11/2011 | Sampognaro et al. |
| 2012/0143237 A1 | 6/2012 | Cam et al. |
| 2012/0143317 A1 | 6/2012 | Cam et al. |
| 2012/0245674 A1 | 9/2012 | Molaei et al. |
| 2012/0290067 A1 | 11/2012 | Cam et al. |
| 2012/0296361 A1 | 11/2012 | Cam et al. |
| 2013/0090682 A1 | 4/2013 | Bachman et al. |
| 2013/0204290 A1 | 8/2013 | Clarke et al. |
| 2013/0268046 A1 | 10/2013 | Gerberding et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |
| 2013/0304109 A1 | 11/2013 | Abrams et al. |
| 2014/0052233 A1 | 2/2014 | Cox et al. |
| 2014/0058420 A1 | 2/2014 | Hannes et al. |
| 2014/0121752 A1 | 5/2014 | Losordo et al. |
| 2014/0128901 A1 | 5/2014 | Kang et al. |
| 2014/0142608 A1 | 5/2014 | Eskridge et al. |
| 2014/0180377 A1 | 6/2014 | Bose et al. |
| 2015/0039015 A1 | 2/2015 | Gerberding |
| 2015/0142025 A1 | 5/2015 | Brandeis |
| 2015/0142042 A1 | 5/2015 | Cox |
| 2015/0142043 A1 | 5/2015 | Furey |
| 2015/0157329 A1 | 6/2015 | Rudakov et al. |
| 2015/0157331 A1 | 6/2015 | Levy et al. |
| 2015/0164512 A1 | 6/2015 | Chin et al. |
| 2015/0164665 A1 | 6/2015 | Cam et al. |
| 2015/0182361 A1 | 7/2015 | Ferrera et al. |
| 2015/0196305 A1 | 7/2015 | Meyer et al. |
| 2015/0216534 A1 | 8/2015 | Riina et al. |
| 2015/0216687 A1 | 8/2015 | Gerberding et al. |
| 2015/0245932 A1 | 9/2015 | Molaei et al. |

(56) References Cited

U.S. PATENT DOCUMENTS

| | | |
|---|---|---|
| 2015/0250628 A1 | 9/2015 | Monstadt et al. |
| 2015/0282962 A1 | 10/2015 | Strauss et al. |
| 2015/0327867 A1 | 11/2015 | Bachman et al. |
| 2015/0342612 A1 | 12/2015 | Wu et al. |
| 2016/0015395 A1 | 1/2016 | Molaei et al. |
| 2016/0015396 A1 | 1/2016 | Cox et al. |
| 2016/0030050 A1 | 2/2016 | Franano et al. |
| 2016/0038153 A1 | 2/2016 | Losordo et al. |
| 2016/0249936 A1 | 9/2016 | Clarke et al. |

FOREIGN PATENT DOCUMENTS

| | | |
|---|---|---|
| CN | 1399530 A | 2/2003 |
| CN | 1399531 A | 2/2003 |
| CN | 101489492 A | 7/2009 |
| CN | 102202585 A | 9/2011 |
| CN | 102762156 A | 10/2012 |
| CN | 103230290 A | 8/2013 |
| CN | 103381101 A | 11/2013 |
| CN | 103582460 A | 2/2014 |
| DE | 10200802830 A1 | 4/2009 |
| DE | 102008028308 | 4/2009 |
| EP | 0820726 A2 | 1/1998 |
| EP | 1269935 A2 | 1/2003 |
| EP | 1527753 A2 | 5/2005 |
| EP | 2326259 A1 | 6/2011 |
| EP | 2451363 A2 | 5/2012 |
| EP | 2713904 A1 | 4/2014 |
| HK | 1134421 A1 | 3/2014 |
| JP | 2001286478 A | 10/2001 |
| JP | 2002516705 A | 6/2002 |
| JP | 2003512129 A | 4/2003 |
| JP | 2005522266 A | 7/2005 |
| JP | 2009512515 A | 3/2009 |
| JP | 2013226419 A | 11/2013 |
| KR | 20080081899 A | 9/2008 |
| WO | WO-9724978 A1 | 7/1997 |
| WO | WO-9726939 A1 | 7/1997 |
| WO | WO-9731672 A1 | 9/1997 |
| WO | WO-9823227 A1 | 6/1998 |
| WO | WO-9850102 A1 | 11/1998 |
| WO | WO-9905977 A1 | 2/1999 |
| WO | WO-9907294 A1 | 2/1999 |
| WO | WO-9915225 A1 | 4/1999 |
| WO | WO-0013593 A1 | 3/2000 |
| WO | WO-0130266 A1 | 5/2001 |
| WO | WO-2001093782 | 12/2001 |
| WO | WO02/00139 | 1/2002 |
| WO | WO-2002000139 | 1/2002 |
| WO | WO-0213899 A1 | 2/2002 |
| WO | WO-02071977 | 9/2002 |
| WO | WO-02078777 | 10/2002 |
| WO | WO-02087690 | 11/2002 |
| WO | WO-03059176 A2 | 7/2003 |
| WO | WO-03075793 A1 | 9/2003 |
| WO | WO-04019790 A1 | 3/2004 |
| WO | WO-04026149 A1 | 4/2004 |
| WO | WO-04105599 A1 | 12/2004 |
| WO | WO-05033409 A1 | 4/2005 |
| WO | WO-05082279 A1 | 9/2005 |
| WO | WO-2006119422 A2 | 11/2006 |
| WO | WO-2007/047851 A2 | 4/2007 |
| WO | WO-2008/151204 A1 | 12/2008 |
| WO | WO-2010/028314 A1 | 3/2010 |
| WO | WO-2011029063 A2 | 3/2011 |
| WO | WO-2012167137 A1 | 12/2012 |
| WO | WO-2012167156 A1 | 12/2012 |
| WO | WO-2013052920 A1 | 4/2013 |
| WO | WO-2013169380 A1 | 11/2013 |
| WO | WO-2014029835 A1 | 2/2014 |
| WO | WO-2015179377 A1 | 11/2015 |

OTHER PUBLICATIONS

Cordis NeuroVascular, Inc.; "Prolwer Select Plus Microcatheter," Product Brochure; No. 154-9877-1; Miami Lakes, FL, USA (2003).

Cordis NeuroVascular, Inc.; "Prowler Select LP Microcatheter," Product Brochure; No. 155-5585; Miami Lakes, FL, USA (2004).

Cordis NeuroVascular, Inc.; "Rapid Transit Microcatheter," Product Brochure; No. 152-7369-2; Miami Lakes, FL, USA (2003).

Extended European Search Report, European Application No. 06826291.4, dated Nov. 19, 2009, 7 pages.

Gupta et al. SMST-2003: Proc. Intl. Conf. Shape Memory Superelastic Technol.; Pacific Grove, CA; p. 639; 2003.

International Search Report and Written Opinion for International Application PCT/US2013/031793, dated Jun. 26, 2013, 14 pages.

International Search Report and Written Opinion for Application No. PCT/US2010/047908, dated May 25, 2011.

International Search Report and Written Opinion for International Application No. PCT/US2009/056133, dated Oct. 26, 2009, 11 pages.

International Search Report and Written Opinion for International Application No. PCT/US2010/047908, dated Mar. 15, 2012, 11 pages.

International Search Report and Written Opinion for International Application No. PCT/US2012/040552, dated Aug. 28, 2012, 14 pages.

International Search Report and Written Opinion for International Application PCT/US2012/040536, dated Oct. 15, 2012, 17 pages.

International Search Report and Written Opinion for International Application PCT/US2012/040558, dated Oct. 8, 2012, 17 pages.

International Search Report and Written Opinion for International Application PCT/US2012/059133, dated Mar. 11, 2013, 15 pages.

International Search Report for International Application No. PCT/US06/40907, dated May 1, 2008, 2 pages.

Micrus Copr.; "Concourse 14 Microcatheter" Product Brochure; Sunnyvale ,CA, USA.

Polytetraflouroethylene Implants, DermNet NZ, Nov. 11, 2005, http://dermetnz.org/polytetrafluoroethylene.html.

Singapore Examination Report for Singapore Application No. 200802811-0, dated Jul. 12, 2009, 7 pages.

\* cited by examiner

SYSTEMS AND METHODS FOR ENCLOSING AN ANATOMICAL OPENING, INCLUDING SHOCK ABSORBING ANEURYSM DEVICES

CROSS-REFERENCE TO RELATED APPLICATION

The present application is a U.S. National Stage of International Application No. PCT/US2012/040552, filed Jun. 1, 2012, entitled "SYSTEMS AND METHODS FOR ENCLOSING AN ANATOMICAL OPENING, INCLUDING SHOCK ABSORBING ANEURYSM DEVICES," and claims the benefit of U.S. Provisional Patent Application No. 61/493,348, filed Jun. 3, 2011, both of which are incorporated herein by reference in their entirety.

TECHNICAL FIELD

The present technology relates to implantable therapeutic devices and methods for endovascular placement of devices at a target site, such as an opening at a neck of an aneurysm. For example, selected embodiments of the present technology comprise shock absorbing structures that can inhibit dislodgement of the device relative to the aneurysm.

BACKGROUND

Many of the currently available surgical approaches for closing openings and repairing defects in anatomical lumens and tissues (e.g., blood vessels), septal defects, and other types of anatomical irregularities and defects are highly invasive. Surgical methods for clipping brain aneurysms, for example, require opening the skull, cutting or removing overlying brain tissue, clipping and repairing the aneurysm from outside the blood vessel, and then reassembling tissue and closing the skull. The risks related to anesthesia, bleeding, and infection associated with these types of procedures are high, and tissue that is affected during the procedure may or may not survive and continue functioning.

Minimally invasive techniques for treating aneurysms are accordingly highly desirable. In general, such minimally invasive therapeutic techniques help prevent material that collects or forms in the aneurysm cavity from entering the bloodstream and help prevent blood from entering and collecting in the aneurysm. This is often accomplished by introducing various materials and devices into the aneurysm. For example, implantable vaso-occlusive metallic structures are well known and commonly used. Many conventional vaso-occlusive devices have helical coils constructed from a shape memory material or noble metal that forms a desired coil configuration upon exiting the distal end of a delivery catheter. The function of the coil is to fill the space formed by an anatomical defect and to facilitate the formation of an embolus with the associated allied tissue. Multiple coils of the same or different structures may be implanted serially in a single aneurysm or other vessel defect during a procedure. Implantable framework structures are also used in an attempt to stabilize the wall of the aneurysm or defect prior to insertion of filling material such as coils. It is important to accurately implant vaso-occlusive devices within the internal volume of a cavity and to maintain the devices within the internal volume of the aneurysm. Migration or projection of a vaso-occlusive device from the cavity may interfere with blood flow or nearby physiological structures and can pose a serious health risk.

In addition to the difficulties of delivering implantable occlusion devices, some types of aneurysms are challenging to treat because of the particularities of the treatment site and/or the structural features of the aneurysm itself. Wide-neck aneurysms, for example, are known to present particular difficulty in the placement and retention of vaso-occlusive coils. Aneurysms at sites of vascular bifurcation are another example where the anatomical structure poses challenges to methods and devices that are effective in treating the typical sidewall aneurysms. It is therefore challenging to position conventional implantable devices during deployment, prevent shifting or migration of such devices after deployment, and preserve blood flow in neighboring vessels following deployment.

DETAILED DESCRIPTION

The present disclosure describes implantable therapeutic devices and methods for endovascular placement of devices at a target site, such as an opening at a neck of an aneurysm. In particular, selected embodiments of the present technology comprise shock absorbing structures that can inhibit dislodgement of the device relative to the aneurysm. The following description provides many specific details for a thorough understanding of, and enabling description for, embodiments of the disclosure. Well-known structures, systems, and methods often associated with such systems have not been shown or described in detail to avoid unnecessarily obscuring the description of the various embodiments of the disclosure. In addition, those of ordinary skill in the relevant art will understand that additional embodiments may be practiced without several of the details described below.

Figure 1A:
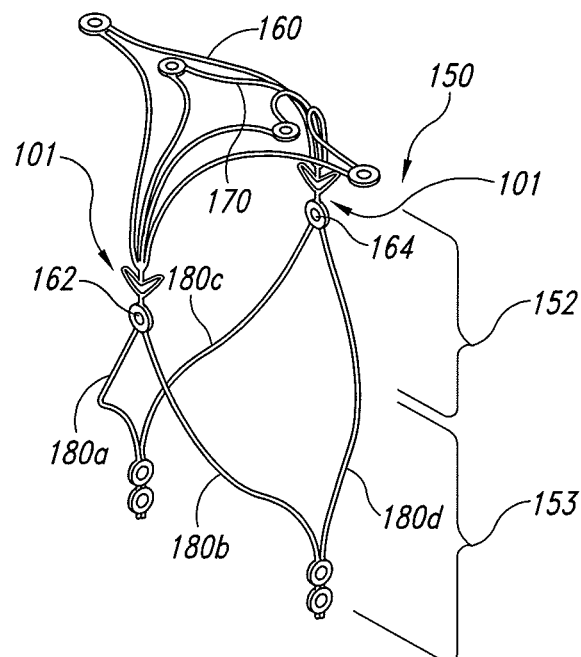
FIGS. 1A-1C are views of an aneurysm device having a shock absorbing structure configured in accordance with an embodiment of the technology.
Figure 1B:
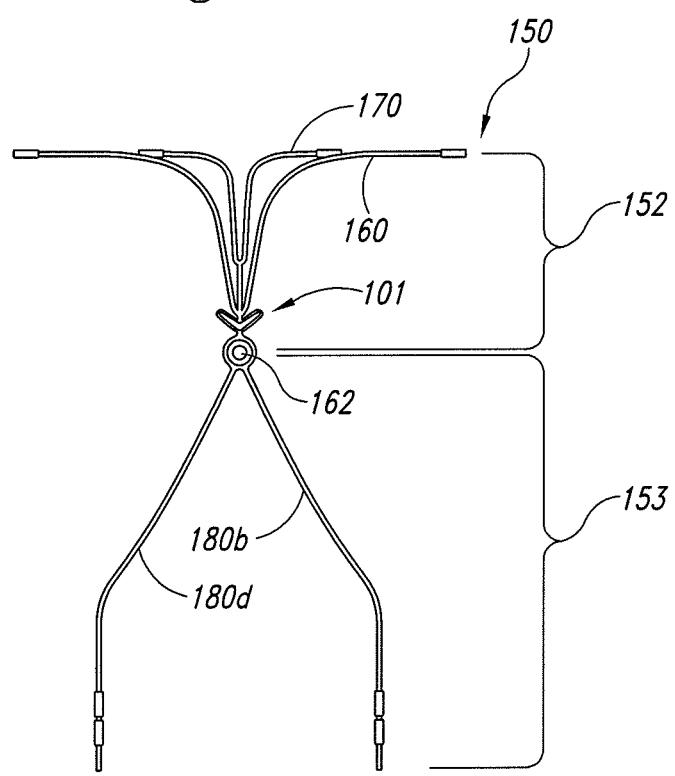
Figure 1C:
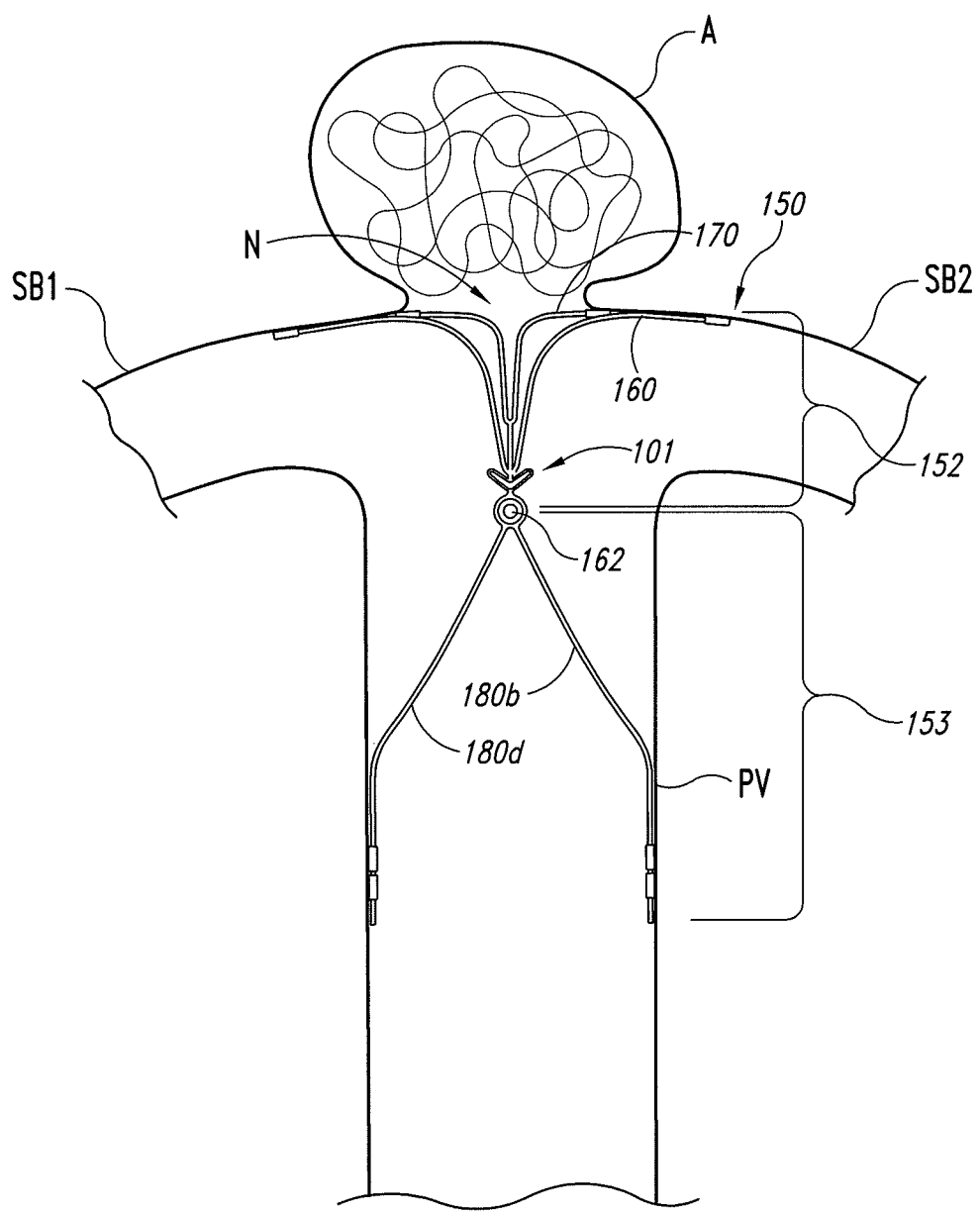

FIGS. 1A-1C are views of an aneurysm device 150 having a shock absorbing structure configured in accordance with an embodiment of the technology. In particular, FIG. 1A is an isometric view of the aneurysm device 150 and FIG. 1B is a front view of the device 150 outside of a patient, and FIG. 1C is a partially schematic view of the device 150 at a treatment site proximate to an aneurysm A in a patient. Referring to FIGS. 1A-1C together, the aneurysm device 150 comprises a closure structure 152, one or more shock absorbing structures 101 (two are shown in the illustrated embodiment), and a supplemental stabilizer or support 153 extending from the closure structure 152 and the shock absorbing structures 101.

The closure structure 152 can be a frame, scaffold, or other structure that at least partially occludes the neck N of the aneurysm A to prevent embolic coils (shown in FIG. 1C) or other coagulative material within the aneurysm A from escaping into the bloodstream. The proximally-extending sides of the closure structure 152 and the supplemental stabilizer 153 hold the curved portion of the closure structure 152 at the neck N of the aneurysm A. The closure structure 152 includes a perimeter support 160 and an inner support 170. The supports 160 and 170 can have a rhombuslike (e.g., diamond-shaped) shape or configuration. The perimeter support 160 and inner support 170 can be joined at junctions 162 and 164. The aneurysm device 150 can also have struts 180a-d projecting proximally from the junctions 162 and 164. Struts 180a-b are connected at junction 162 and struts 180c-d are connected at junction 164 to form the supplemental stabilizer 153 with proximal anchoring segments.

In multiple device embodiments, the aneurysm device 150 may be deployed such that it is anchored along a specific portion of the neck N of the aneurysm A. As shown in FIG. 1C, for example, the closure portion 152 of the aneurysm device 150 can bridge a portion or all of the neck N and control blood flow into the aneurysm A. The supports 160 and 170 can lodge in side branch vessels SB 1 and SB2, while struts 180a-d can press against a wall of a parent vessel PV to collectively secure placement of the aneurysm device 150. As will be discussed in further detail below with reference to FIG. 2, the shock absorbing structures 101 can smooth out or dampen movement of the aneurysm device 150 relative to the blood vessel walls. Additionally, the shock absorbing structures 101 can enhance the junction of the closure structure 152 to the supplemental stabilizer 153 and can improve the aneurysm device's ability to withstand motion relative to the blood vessel walls.

Figure 2:
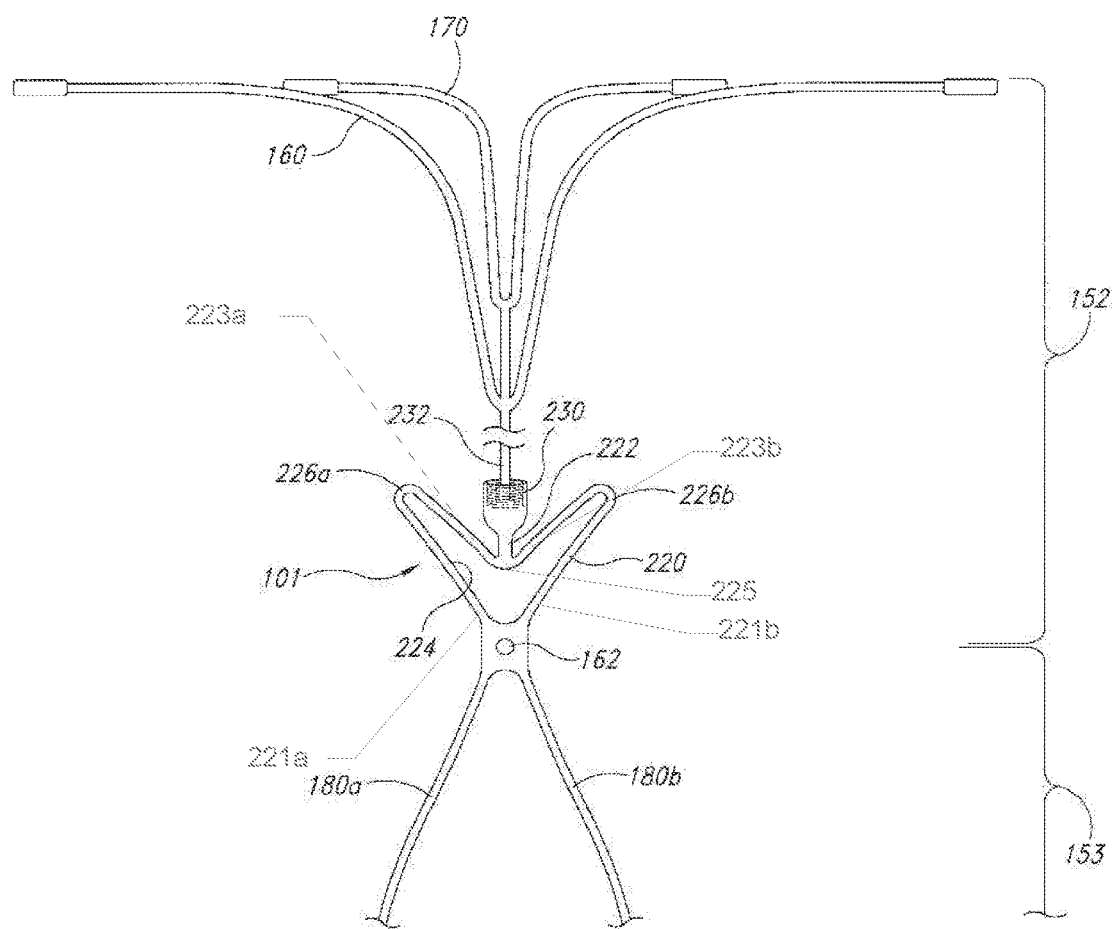
FIG. 2 is a partially schematic illustration of the shock absorbing structure of FIG. 1.

FIG. 2 is a partially schematic illustration of the shock absorbing structure 101. The shock absorbing structure 101 includes a shock absorbing assembly 220 distally coupled to the junction 162 between the closure structure 152 and the supplemental stabilizer 153. In the illustrated embodiment, the shock absorbing assembly 220 comprises a leaf-spring having a first spring arm 226a and a second spring arm 226b extending laterally from the junction 162. The first and second spring arms 226a and 226b can surround an aperture 224. In further embodiments, the shock absorbing assembly 220 can include other types of springs or other shock-absorbing mechanisms. The supplemental stabilizer 153 can move proximally, distally, and/or laterally relative to the closure structure 152 as the shock absorbing assembly 220 contracts and expands.

A proximally-extending portion 232 of the closure structure 152 may be coupled to a distally-extending portion 222 of the shock absorbing structure 101 by an attachment feature 230. In some embodiments, the attachment feature 230 comprises a solder attachment. In further embodiments, however, other attachment mechanisms can be used. The flexibility provided by the shock-absorbing assembly 220 and the attachment feature 230 is expected to inhibit movement of the supplemental stabilizer 153 relative to a vessel wall and help prevent movement in the blood vessel from dislodging the aneurysm device 150 after deployment.

FIG. 2 further illustrates additional details of the shock absorbing structure. The first spring arm 226a can include a first spring arm proximal 221a end and a first spring arm distal end 223a while the second spring art 226b can include a second spring arm proximal end 221b and a second spring arm distal end 223b. The first and the second spring arm proximal ends 221a, 221b can couple to and extend away from the junction 162 at an angle to each other. The first and the second spring arms 226a, 226b can form and at least partially surround the aperture 224. The first and the second spring arm distal ends 223a, 223b meet at the distally-extending portion 222 of the shock absorbing structure 101 to form a generally V-shaped arrangement. The distally-extending portion 222 is proximate to a notch 225 in the generally V-shaped arrangement.

Figure 3:
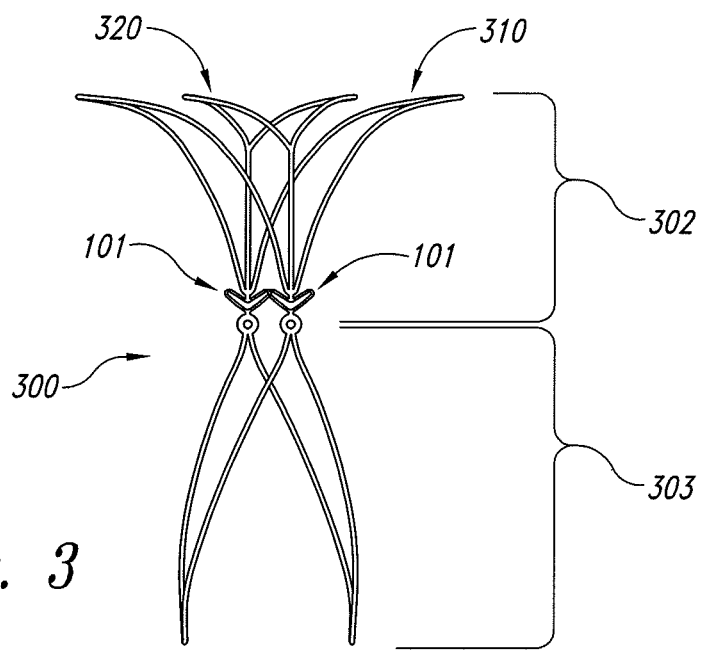
FIG. 3 is a view of an aneurysm device having a shock absorbing structure configured in accordance with an additional embodiment of the technology.
Figure 4:
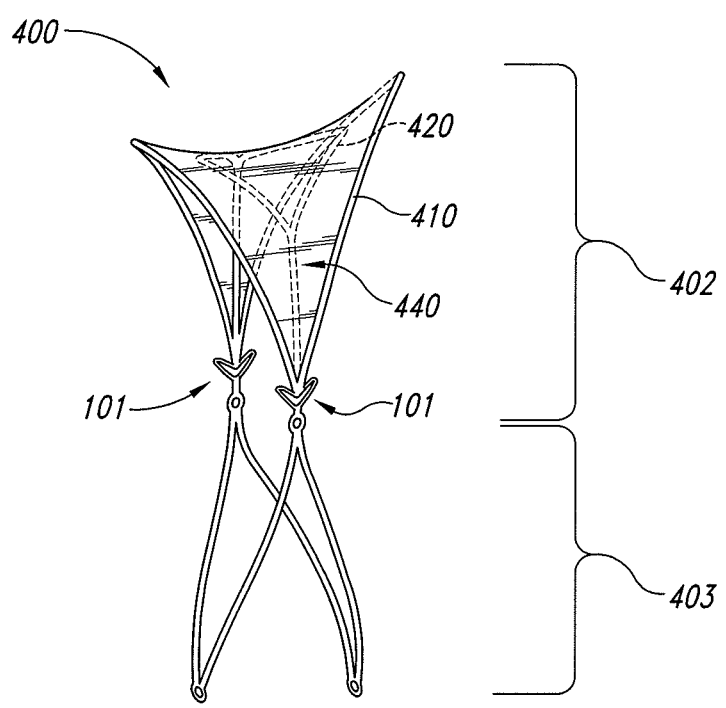
FIG. 4 is a view of an aneurysm device having a shock absorbing structure configured in accordance with an additional embodiment of the technology.

FIGS. 3 and 4 illustrate aneurysm devices having shock absorbing structures configured in accordance with additional embodiments of the technology. The aneurysm devices shown in FIGS. 3 and 4 include several features generally similar to the aneurysm device 150 described above with reference to FIG. 1. Referring to FIG. 3, for example, an aneurysm device 300 includes a closure structure 302 having a perimeter support 310 and an inner support 320. The shock absorbing structure 101 is located at a proximal end of the closure structure 302. The aneurysm device 300 further includes a supplemental stabilizer or support 303 extending from the shock absorbing structure 101. The shock absorbing structure 101 can enhance the junction of the closure structure 302 to the supplemental stabilizer 303 and can improve the aneurysm device's ability to withstand motion within the blood vessel.

Referring now to FIG. 4, an aneurysm device 400 includes a closure structure 402 including a plurality of struts that form a perimeter support 410 and an inner support 420. The aneurysm device 400 includes shock absorbing structures 101 positioned on a proximal end of the closure structure 402 and coupled to a distal end of a supplemental stabilizer 403. The aneurysm device 400 further includes a barrier 440 that covers at least a portion of the perimeter support 410. In the particular embodiment illustrated in FIG. 4, the barrier 440 can be a membrane or other type of cover that extends across the full lateral aspect of the perimeter support 410 and a significant portion of the U-shaped curved region of both the perimeter support 410 and the inner support 420. The barrier 440 can enhance the separation between the cavity of an aneurysm and the lumen of the side branch vessels compared to aneurysm devices without the barrier.

EXAMPLES

Example 1

An aneurysm device endovascularly deliverable to a site proximate to an aneurysm near a parent artery with bifurcating downstream branches, the aneurysm device comprising:

a closure structure comprising a distal-facing aspect configured to at least partially occlude the aneurysm;

a supplemental stabilizer connected to the closure structure, the supplemental stabilizer configured to reside in the parent artery and press outward against a luminal wall thereof; and a shock absorbing structure coupled to a proximal end portion of the closure structure and to a distal end portion of the supplemental stabilizer.

Example 2

The aneurysm device of example 1 wherein the shock absorbing structure comprises a spring.

Example 3

The aneurysm device of example 2 wherein the spring comprises a leaf spring having a first spring arm and a second spring arm, and wherein the first and second spring aims at least partially surround an aperture.

Example 4

The aneurysm device of example 3 wherein the first spring arm and the second spring aim extend laterally from at least one of the closure structure or the supplemental stabilizer.

Example 5

The aneurysm device of example 2 wherein the supplemental stabilizer is configured to move proximally, distally, and/or laterally relative to the closure structure as the shock absorbing assembly exhibits spring movement.

Example 6

The aneurysm device of example 1, further comprising an attachment feature configured to couple the closure structure to the shock absorbing structure.

Example 7

The aneurysm device of example 6 wherein the attachment feature comprises hardened solder.

Example 8

The aneurysm device of example 1 wherein the shock absorbing structure comprises a moveable junction between the closure structure and the supplemental stabilizer.

Example 9

A system for treating an aneurysm, the system comprising:
a distal framework portion comprising a distal-facing aspect configured to enclose the aneurysm;
a proximal support framework connected to the distal framework portion, the support framework configured to reside in a parent artery and biased to press outward against a luminal wall thereof; and
a spring coupled to the distal framework portion and proximally movable relative to the distal framework portion.

Example 10

The system of example 9 wherein the spring comprises a junction connecting the distal framework portion and the proximal support framework.

Example 11

The system of example 9 wherein the spring comprises a leaf spring.

Example 12

The system of example 9 wherein the distal framework portion comprises a set of distal struts forming at least one quadrilateral form with first and second longitudinal junctions, and wherein the system further comprises a barrier covering at least a portion of the distal struts.

Example 13

The system of example 9 wherein the barrier comprises a membrane configured to enhance a separation between a cavity of the aneurysm and the parent artery.

Example 14

A method of treating an aneurysm located at a site within a blood vessel, the method comprising:
positioning a framework comprising a distal portion and a proximal portion at a site proximate to the aneurysm;
applying a force outward from the proximal portion of the framework against a luminal wall of the blood vessel, and
absorbing movement of the framework relative to the blood vessel with a shock absorbing structure operably coupled with the framework.

Example 15

The method of example 14 wherein absorbing movement of the framework comprises dampening movement of the framework relative to a blood vessel wall with the shock-absorbing structure.

Example 16

The method of example 14 wherein absorbing movement of the framework comprises absorbing movement with a spring connecting the distal portion and the proximal portion.

Example 17

The method of example 14 wherein absorbing movement of the framework comprises inhibiting dislodgement of the framework relative to the aneurysm.

Example 18

The method of example 14 wherein absorbing movement of the framework comprises absorbing movement with a leaf spring.

Example 19

The method of example 14 wherein absorbing movement of the framework comprises absorbing movement of the distal portion relative to the proximal portion.

Example 20

The method of example 14, further comprising at least partially occluding the aneurysm with a barrier membrane coupled to the distal portion.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. In particular, the clot removal devices described above with reference to particular embodiments can include one or more additional features or components, or one or more of the features described above can be omitted.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, B all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An aneurysm device endovascularly deliverable to a site proximate to an aneurysm near a parent artery with bifurcating downstream branches, the aneurysm device comprising:
   a closure structure comprising a distal-facing aspect configured to at least partially occlude the aneurysm;
   a supplemental stabilizer connected to the closure structure, the supplemental stabilizer configured to reside in the parent artery and press outward against a luminal wall thereof;
   a junction between the closure structure and the supplemental stabilizer; and
   a shock absorbing structure coupled to a proximal end portion of the closure structure and to a distal end portion of the supplemental stabilizer, comprising:
      a first spring arm comprising a first spring arm proximal end and a first spring arm distal end; and
      a second spring arm comprising a second spring arm proximal end and a second spring arm distal end;
      wherein the first and second spring arm proximal ends are coupled to each other at the junction,
      wherein the first spring arm and the second spring arm extend away from the junction at an angle to each other,
      wherein the first and the second spring arms at least partially surround an aperture,
      wherein the first and the second spring arms act as a leaf spring,
      wherein the first and the second spring arm distal ends meet at a distally-extending portion of the shock absorbing structure to form a generally V-shaped arrangement and the distally-extending portion is proximate to a notch in the generally V-shaped arrangement, and
      wherein the proximal end portion of the closure structure coupled to the distally-extending portion of the shock absorbing structure.

2. The aneurysm device of claim 1 wherein the supplemental stabilizer is configured to move proximally, distally, and/or laterally relative to the closure structure as the shock absorbing assembly exhibits spring movement.

3. The aneurysm device of claim 1, further comprising an attachment feature configured to couple the closure structure to the shock absorbing structure.

4. The aneurysm device of claim 3 wherein the attachment feature comprises hardened solder.

5. A system for treating an aneurysm, the system comprising:
   a distal framework portion comprising a distal-facing aspect configured to enclose the aneurysm;
   a proximal support framework connected to the distal framework portion, the support framework configured to reside in a parent artery and biased to press outward against a luminal wall thereof; and
   a spring coupled to the distal framework portion and proximally movable relative to the distal framework portion, wherein the spring comprises:
      a first spring arm comprising a first spring arm proximal end and a first spring arm distal end;
      a second spring arm comprising a second spring arm proximal end and a second spring arm distal end; and
      a junction between the distal framework portion and the proximal support framework,
      wherein the first spring arm and the second spring arm extend away from the junction and toward the distal framework portion such that the first spring arm and the second spring arm have a generally V-shaped arrangement formed from the first and the second spring arm proximal ends meeting at the junction and the first and the second spring arm distal ends meeting at the distal framework portion, and
      wherein a proximal portion of the distal framework portion resides proximate to a notch in the generally V-shaped arrangement between the first and second spring arms.

6. The system of claim 5 wherein the junction connects the distal framework portion and the proximal support framework.

7. The system of claim 5 wherein the distal framework portion comprises a set of distal struts forming at least one quadrilateral form with first and second longitudinal junctions, and wherein the system further comprises a barrier covering at least a portion of the distal struts.

8. The system of claim 7 wherein the barrier comprises a membrane configured to enhance a separation between a cavity of the aneurysm and the parent artery.

9. A method of treating an aneurysm located at a site within a blood vessel, the method comprising:
   positioning a framework comprising a distal portion and a proximal portion at a site proximate to the aneurysm;
   applying a force outward from the proximal portion of the framework against a luminal wall of the blood vessel;
   absorbing movement of the framework relative to the blood vessel with a generally V-shaped spring connecting the distal portion and the proximal portion of the framework; and
   disposing a section of the distal portion within a notch in the generally V-shaped spring, wherein the generally V-shaped spring comprises a first spring arm and a second spring arm; wherein the first spring arm comprises a first spring arm proximal end and a first spring arm distal end; wherein the second spring arm comprises a second spring arm proximal end and a second spring arm distal end, wherein the first and the second spring arm proximal ends are coupled at a junction; wherein the first spring arm and second spring arm extend away from the junction at an angle to each other, wherein the first and the second spring arms at least partially surround an aperture, wherein the first and the second spring arms act as a leaf spring, and wherein the first and the second spring arm distal ends meet at a distally-extending portion to form a generally V-shaped arrangement and the distally-extending portion is proximate to a notch in the generally V-shaped arrangement.

10. The method of claim 9 wherein absorbing movement of the framework comprises inhibiting dislodgement of the framework relative to the aneurysm.

11. The method of claim 9 wherein absorbing movement of the framework comprises absorbing movement with the leaf spring.

12. The method of claim 9, further comprising at least partially occluding the aneurysm with a barrier membrane coupled to the distal portion.

* * * * *